United States Patent
Hesse et al.

(10) Patent No.: US 8,338,194 B2
(45) Date of Patent: Dec. 25, 2012

(54) METHOD FOR THE IN-SITU DETERMINATION OF THE MATERIAL COMPOSITION OF OPTICALLY THIN LAYERS

(75) Inventors: Raik Hesse, Berlin (DE); Hans-Werner Schock, Stuttgart (DE); Daniel Abou-Ras, Berlin (DE); Thomas Unold, Potsdam (DE)

(73) Assignee: Helmholtz-Zentrum Berlin fuer Materialien und Energie GmbH, Berlin (DE)

( * ) Notice: Subject to any disclaimer, the term of this patent is extended or adjusted under 35 U.S.C. 154(b) by 233 days.

(21) Appl. No.: 12/669,714

(22) PCT Filed: Jul. 9, 2008

(86) PCT No.: PCT/DE2008/001130
§ 371 (c)(1), (2), (4) Date: Jul. 6, 2010

(87) PCT Pub. No.: WO2009/012748
PCT Pub. Date: Jan. 29, 2009

(65) Prior Publication Data
US 2010/0291714 A1    Nov. 18, 2010

(30) Foreign Application Priority Data

Jul. 20, 2007 (DE) .......................... 10 2007 034 289

(51) Int. Cl.
*H01L 21/66* (2006.01)
(52) U.S. Cl. ........................................................ 438/16
(58) Field of Classification Search .................... 438/16, 438/29, 31, 32
See application file for complete search history.

(56) References Cited

U.S. PATENT DOCUMENTS

| | | | |
|---|---|---|---|
| 5,450,250 A | 9/1995 | Garcia et al. | |
| 6,466,604 B1 | 10/2002 | Kopf | |

(Continued)

FOREIGN PATENT DOCUMENTS

| | | |
|---|---|---|
| DE | 19723729 A1 | 12/1998 |
| DE | 10256909 B3 | 7/2004 |
| DE | 69917899 T2 | 8/2005 |
| DE | 102005023735 A1 | 11/2006 |
| DE | 102005023737 A1 | 11/2006 |

(Continued)

OTHER PUBLICATIONS

Sakurai K et al: "In situ diagnostic methods for thin-film fabrication: utilization of heat radiation and light scattering" Progress in Photovoltaics: Research Andapplications, vol. 12, No. 2-3, Mar. 2004, pp. 219-234.

(Continued)

*Primary Examiner* — Thao Le
(74) *Attorney, Agent, or Firm* — Leydig, Voit & Mayer, Ltd.

(57) ABSTRACT

A method for in situ determination of a material composition of optically thin layers deposited from a vapor phase onto a substrate includes irradiating the substrate with incoherent light of at least three different wavelengths, optically detecting in a spatially resolved manner a reflection intensity of a diffuse or a direct light scattering emanating from a deposited layer outside of a total reflection, concurrently providing numerical values of the detected reflection intensity to an optical layer model based on general line transmission theory, ascertaining values for the optical layer parameters of the deposited layer from the optical layer model for the at least three different wavelengths by numerically adapting the optical layer model to a time characteristic of the detected reflection intensities, and quantitatively determining a material composition of the deposited layer from the ascertained values by comparing the ascertained values to standard values.

11 Claims, 9 Drawing Sheets

U.S. PATENT DOCUMENTS

| | | | |
|---|---|---|---|
| 6,815,235 | B1 | 11/2004 | Markle |
| 6,891,627 | B1 | 5/2005 | Levy et al. |
| 7,033,070 | B2 | 4/2006 | Azami |
| 7,271,896 | B2 * | 9/2007 | Chan et al. .................... 356/301 |
| 7,569,487 | B2 * | 8/2009 | Mieno .......................... 438/707 |

FOREIGN PATENT DOCUMENTS

| | | | |
|---|---|---|---|
| DE | 102006016132 A1 | 3/2007 |
| DE | 10 2005 050 795 A1 | 4/2007 |
| EP | 146177 A1 | 6/1985 |
| EP | 1435517 A1 | 7/2004 |
| EP | 1467177 A1 | 10/2004 |
| WO | 96/36909 A1 | 11/1996 |
| WO | WO 9636906 A1 | 11/1996 |

OTHER PUBLICATIONS

Hesse R et al: "A reliable optical method for in situ process control for deposition of Cu(In,Ga)Se2 thin layers for photovoltaics" Proceedings of the SPIE—The International Society for Optical Engineering SPIE—The International Society for Optical Engineering USA, vol. 6651, No. 1, Sep. 13, 2007, pp. 665108-1-66518-9.

R. Scheer et al.: "Cu(In1-xGax)Se2 growth studies by in situ spectroscopic light scattering" Applied Physics Letters 82 (2003), pp. 2091-2093.

International Search Report mailed Jan. 13, 2009, which issued during the prosecution of International Patent Application No. PCT/DE2008/001130; 6 pages.

* cited by examiner

METHOD FOR THE IN-SITU DETERMINATION OF THE MATERIAL COMPOSITION OF OPTICALLY THIN LAYERS

CROSS REFERENCE TO RELATED APPLICATIONS

This application is a U.S. National Phase application under 35 U.S.C. §371 of International Application No. PCT/DE2008/001130, filed Jul. 9, 2008, and claims benefit to German patent application DE 10 2007 034 289.8, filed Jul. 20, 2007. The International Application was published in German on Jan. 29, 2009 as WO 2009/012748 A2 under PCT Article 21 (2).

FIELD

The present invention relates to a method for in situ determining the material composition of optically thin layers that are deposited from the vapor phase onto a substrate, there being an interferometrically analyzable correlation among the optical layer parameters (complex refractive index $n_{complex}$ having a real part: refractive index $n_{layer}$ and imaginary part: absorption coefficient $K_{layer}$ and real layer thickness $d_{layer}$), as well as to systems for implementing the method and uses thereof.

BACKGROUND

German Patent Publication No. DE 699 17 899 T2 describes using reflectance spectrometry to determine the doping of a silicon wafer. Reference and sample measurements are taken and calculated using physical calculation methods to determine the complex refractive index and the thickness of an optically thin layer. The formulas for the optical reflection of radiation are described in detail, making comprehensible the modeling of the layer to be measured. In this case, however, precise measurements can only be taken ex situ. The measurements are performed in the infrared region since the observed layers are within a thickness range that necessitates IR measurement to permit analysis of an interferometric wave to determine thickness.

A method for in situ determining the optical layer constants of layers in the context of plasma- and ion beam-assisted etching and coating is described in German Patent Application DE 197 23 729 A1. It describes a method for determining the optical constants from the reflection of light produced by the characteristic radiation of the sources used for surface finishing. During the surface finishing process, the reflection spectra are recorded from occurring interferences. Four different wavelengths are individually detected using a wavelength filter. The absolute (real) thickness of the layer is determined from the measurement signals of the normalized radiation. However, this method is only applicable to systems which use a plasma or an ion beam for surface finishing since the plasma or ion beam intensity must be additionally recorded. The substrate itself is not measured. A normalized refractive index is measured whose real value is subsequently determined. The formulas used correspond here to the Fresnel laws for a three-layer system (air—non-absorbing medium—substrate) and are limited thereto.

The European Patent Application EP 1 435 517 A1 describes using spectroscopic ellipsometers for sensing thin multilayer systems. However, ellipsometry only functions reliably in the context of very smooth layers. Moreover, an ellipsometric measurement is only possible ex situ since a polarization measurement method is needed to analyze the reflection. The polarization of the incident light is varied to allow analysis of the resultant influence on the reflected radiation. The complex refractive index is determined by varying the wavelength in a defined manner. The method is performed on multilayer systems using an optical model that is based, however, on numerically adapting (fitting) a frequency-dependent function of thickness and refractive index (similar to FFT, fast Fourier transformation).

A thickness measurement method for multilayer systems is likewise described in European Patent Application EP 1 467 177 A1. This method is based on an ex situ measurement, followed by a subsequent analysis based on a Fourier transformation. In the process, the sample is irradiated with light, and a frequency spectrum is generated by the FFT. The thickness of the individual layers is determined by analyzing the peaks of the FFT. A CCD (charge-coupled device) is used as a spatially resolving optical detector for different wavelengths.

German Patent Application DE 10 2005 023 735 A1 describes an ex situ method for automatically performing a surface examination, which provides for adapting a theoretical curve to a measuring curve using an FFT or a gradient method. In this context, however, layer thicknesses of over 10 μm are observed that are no longer to be classified as optically thin layers. The reflection spectrum is compared to a calculated spectrum. In addition, an FFT spectrum is exclusively analyzed, and the occurring peaks of this spectrum are observed. The number of layers is determined on the basis of the FFT spectrum. Thus, the layer must already be finish-processed since it would otherwise not be possible to record this type of spectrum. Different approximation methods are then derived from this spectrum.

The German Patent Application DE 10 2005 023 737 A1 describes a method for determining the layer thickness or the refractive index of a thin layer from the total reflection. It discusses determining a layer thickness or a dispersion parameter from a reflection spectrum. To this end, the measurement is compared to a model spectrum. However, only the actually changed layer is observed, the model used not being further clarified.

The aforementioned publications relate to the analysis of reflections of optical radiation in the context of smooth surfaces. All of the methods are based on the measurement of total reflection and thus require a normalization either by measuring the reference light or by subsequently measuring the refractive index using other methods. The optical models used are based on the use of Fresnel equations. No method is used to control a material vaporization process to obtain an optically thin layer.

A method employing processes for depositing chalcopyrite thin layers on moving substrates is described, for example, in German Examined Accepted Specification DE 102 56 909 B3. As a light source, a laser emitting coherent light of one wavelength is directed at a moving substrate in order to control the process of depositing and forming a chalcopyrite thin layer. In this method, the control is based on the scattering of laser light on rough surfaces. The process of vapor depositing $Cu(In,Ga)Se_2$ layers is divided into three stages. Stage I encompasses the vaporization of indium and gallium (co-vaporization or sequential vaporization); stage II the co-vaporization of copper; and stage III the co-vaporization of indium and gallium. In addition, selenium is vaporized during the entire process. The substrate is comprehensively described in terms of material (glass, titanium or plastics) and properties. Various concepts for substrate motion are presented (pass through, rotation, roll-to-roll). Concepts are described for moving the laser that is used. Using the described method, it is possible to implement the process in a controlled manner. In the described method, the process control is based on laser light scattering (LLS) and utilizes individual characteristic points. In this context, the scatter signals of the laser light are recorded during the individual stages. In particular, the scatter signals of the second stage are utilized to estimate stoichiometric ratios in the deposited layer. However, this control does not allow a reproducible implementation of a process since this would require a feedback control with knowledge of the numerical values of the optical layer parameters. Only a qualitative monitoring of the process takes place. In the case of qualitative deviations, the production parameters "temperature of the vaporization source" and "velocity of the substrate" are varied accordingly.

In publication I by R. Scheer et al.: "Cu(In$_{1-x}$,Ga$_x$)Se$_2$ growth studies by in situ spectroscopic light scattering" (Applied Physics Letters 82 (2003), pp. 2091-2093), the LLS method is expanded to include a spectral light scattering (SLS) to be able to recognize the dependency between the roughness of the deposited layer and the scatter signal. Coherent laser light functions only in the context of rough surfaces. For smooth surfaces, as are typically present in the substrate at the beginning of the process, no analyzable measurement signals are produced. For the SLS, a white light source is used instead of a laser, and an SSD spectrometer is used as a detector. A process control based on the SLS method is likewise described in publication II by K. Sakurai et al.: "In situ diagnostic methods for thin-film fabrication: utilization of heat radiation and light scattering" (Progress in Photovoltaics: Research and Applications 12 (2004), pp. 219-234), upon which the present invention is based as the most proximate related art. However, a process control is not discussed. Here as well, the numerical values of the optical layer parameters are not known, so that the growth of thin layers cannot be quantitatively controlled, and, therefore, the actual values of the control variables (optical layer parameters) cannot be controlled to the nominal values by adjusting the manipulated variables (process parameters).

One option for quantitatively controlling the growth of thin layers is indicated, for example, in U.S. Pat. No. 5,450,250. In this method, interferometric measurements for determining the thickness of an optically thin layer are performed with the aid of a laser and a CCD camera. A laser is used to illuminate the surface of a silicon substrate. Reflections of the incident laser beam are recorded and analyzed by a CCD camera. The method is based on interferometry (compare German Patent Applications DE 10 2005 050 795 A1 and DE 10 2006 016 132 A1). In this case, incident and reflected beams are superimposed on one another in a manner that, in the extreme case, can be destructive or constructive. Absolute thicknesses of thin layers can be thereby determined A determination is only possible, however, when the optical properties of the measured material are sufficiently known. To that end, it is necessary that the magnitude of the complex refractive index be known, in particular. Moreover, it is not taken into consideration that the mentioned material properties are frequently subject to changes during the deposition process. Thus, the mentioned method provides only one fundamental possibility for quantitative process control and one possible feedback control.

For a process control in the sense of a true control loop, it is essential that the components to be controlled be rendered measurable, as is described, for example, in U.S. Pat. No. 7,033,070 B2. To monitor a crystal growth method (floating zone method) for obtaining single crystal silicon, the temperature of the molten silicon is monitored using a CCD camera. In this method, the grown crystal is locally heated by a halogen lamp. The camera is aimed at the crystal region that is heated by the halogen lamp. The CCD camera measures the luminosity of the melt, while filtering the reflected and scattered light of the light source, and thereby estimates the temperature. For this purpose, the CCD camera is equipped with filters to make the infrared light visible. Thus, the method numerically monitors silicon melts as a function of the characteristic luminosity of the melt. However, this method cannot be used to obtain information on the composition or thickness of the material. Rather, the camera monitors to what extent the crystal to be grown has melted.

SUMMARY

In an embodiment, the present invention provides a method for in situ determination of the material composition of optically thin layers that are deposited from a vapor phase onto a substrate, there being an interferometrically analyzable correlation among optical layer parameters, the optical layer parameters including a wavelength-independent real layer thickness and a complex refractive index having as a real part a refractive index and as an imaginary part an absorption coefficient. The method includes irradiating the substrate on a deposition side with incoherent light of at least three different wavelengths in a visible optical region during a deposition process and optically detecting in a spatially resolved manner a reflection intensity of a diffuse or a direct light scattering emanating from a deposited layer outside of the total reflection in the at least three different wavelengths, while concurrently providing numerical values of the detected reflection intensity to an optical layer model based on a general line transmission theory in which the deposited layer is interpreted as being an electromagnetic conductor having a variable field wave impedance, a propagation constant and a wavelength-independent real layer thickness that is equivalent to the conductor length. Values for the optical layer parameters of the deposited layer are ascertained from the optical layer model for the at least three different wavelengths by numerically adapting the optical layer model to the time characteristic of the detected reflection intensities, the wavelength-independent real layer thickness being used as a reference value. A material composition of the deposited layer is quantitatively determined from the ascertained values of the optical layer parameters by comparing the ascertained values to standard values for optical layer parameters of known material compositions.

BRIEF DESCRIPTION OF THE DRAWINGS

An exemplary embodiment of the present invention will be described in more detail below and is schematically shown in the drawings, in which.

DETAILED DESCRIPTION

Figure 1A:
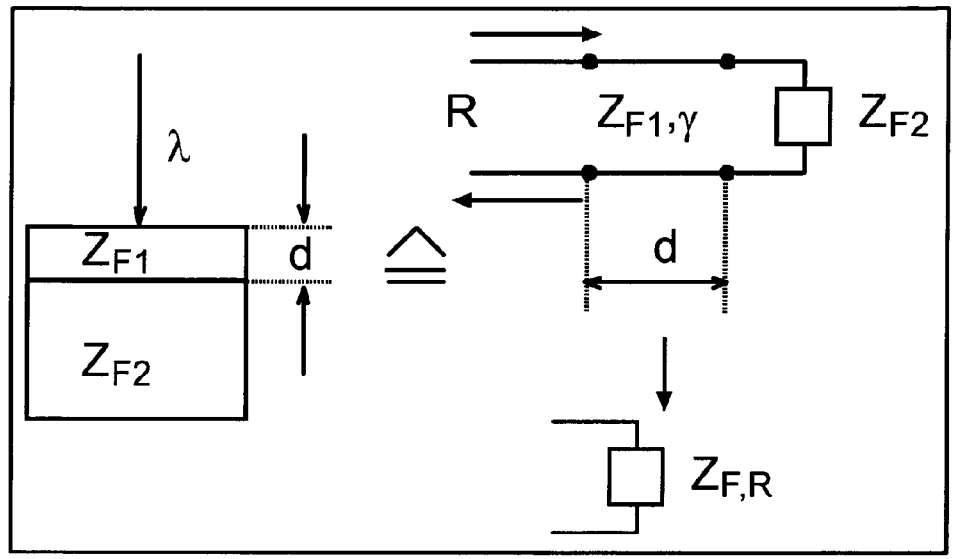
FIG. 1A is a diagram for applying the transmission line theory to optically thin layers.

An object of the present invention is to further refine the method of the species mentioned at the outset for in situ determining the material composition of optically thin layers that are deposited from the vapor phase onto a substrate, there being an interferometrically analyzable correlation among the optical layer parameters, in such a way that the material composition of the deposited layer may be ascertained given knowledge of the optical layer parameters. It is intended, in this connection, that the method be able to be implemented cost-efficiently in real time, without being susceptible to faults. It is intended that one preferred system for implementing the method have components suited for this purpose.

Moreover, it is to be absolutely ensured that highly efficient semiconductor layers for use in photovoltaics be able to be reproducibly produced within a continuous co-vaporization process. In this context, the continuity of the vaporization process leads necessarily to an in situ method which allows a feedback control at any time during the vaporization process. However, to be able to control a process in a closed loop, the control mechanism must be able to function in a manner that is free of errors or interference effects, and the control variables must be measurable. It is likewise necessary that the influence of unavoidable sources of interference be kept at negligibly small levels. Therefore, it should be possible in applications of the inventive method to implement a process control in the sense of a control loop that quantitatively accesses the specific optical layer parameters. For this, it is essential that the components (layer parameters) to be controlled also be rendered measurable.

The method according to an embodiment of the present invention is suited for in situ determining the material composition of optically thin layers that are deposited from the vapor phase onto a substrate. The optically thin layers are those layers for which the complex refractive index $n_{complex}$ (real part: refractive index $n_{layer}$; imaginary part: absorption coefficient $K_{layer}$) and real layer thickness $d_{layer}$ are mutually dependent in that they exhibit an interferometrically analyzable correlation. The limit of the interferometry is reached when the layer is too thick or is too highly absorbent. Optical layers typically have a thickness of up to maximally 10-times the irradiation wavelength, respectively a thickness of less than 1000 nm.

For in situ determining the material composition of such optically thin layers during production thereof, the method according to an embodiment of the present invention encompasses at least the following method steps:

During deposition of the optically thin layer, the substrate is irradiated on the deposition side with incoherent light in the visible optical region. Light of at least three different wavelengths $\lambda_1$, $\lambda_2$, $\lambda_3$ is directed at the deposited layer. Three different wavelengths are needed since there are also three unknown optical layer parameters (refractive index $n_{layer}$, absorption coefficient $K_{layer}$ and layer thickness $d_{layer}$) to be ascertained. Incoherent light may be used both for rough and for smooth surfaces. The use of coherent light is limited to rough surfaces.

The diffuse or direct light scattering emanating from the deposited layer is optically detected in a spatially resolved manner in the three different wavelengths $\lambda_1$, $\lambda_2$, $\lambda_3$. The curve of reflection intensity R as a function of time is measured in each case. However, the incident light is radiated in such a way that no total reflection results. Likewise, no total absorption occurs in the case of the optically thin layers.

In a process carried out concurrently to the measurement, the numerical values of detected reflection intensity R for the different wavelengths $\lambda_1$, $\lambda_2$, $\lambda_3$ are fed into an optical layer model, which is thus implemented in time synchronism with the deposition process. This optical layer model is based on the general transmission line theory from electrical communication engineering. In the method according to an embodiment of the present invention, each deposited layer is interpreted as being an electromagnetic conductor having a variable field wave impedance $Z_G$, a propagation constant $\gamma$ and a real layer thickness $d_{layer}$ that is equivalent to the conductor length.

The optical layer model is numerically analyzed for the different wavelengths $\lambda_1$, $\lambda_2$, $\lambda_3$. By numerically adapting the layer model, respectively the function describing the same, to the time characteristic of the detected reflection intensities, the real values are derived for the optical layer parameters (refractive index $n_{layer}$, absorption coefficient $K_{layer}$, real layer thickness $d_{layer}$) of the deposited layer. In this context, the wavelength-independent real layer thickness $d_{layer}$ is defined as the reference value, so that the method according to an embodiment of the present invention is self-referencing. This eliminates the need for producing an external reference using variables to be additionally acquired.

The actual material composition of the detected deposited layer is then determined from the numerically ascertained values for the optical layer parameters. This is accomplished by making a comparison with standard values for optical layer parameters of known material compositions.

In the event that the material composition changes between different layers, one advantageous embodiment of the method according to an embodiment of the present invention provides that the ascertained values of the optical layer parameters of the preceding layer be stored and used as reference values for a next layer. For that reason, the method according to an embodiment of the present invention may also be used for any given stacks of optically thin layers because it is always the topmost layer that is analyzed as a reference in comparison to the subjacent layers. It may additionally be provided that the reflection intensity resulting from the incident coherent light of one single wavelength be measured (LLS). The influence of the surface roughness of the deposited layer may be hereby considered. However, this requires that a rough surface be present. Smooth surfaces are not able to be analyzed using coherent light.

Further details regarding the specific determinations and specific embodiments of the method according to an embodiment of the present invention and also of the preferred arrangement for implementing the method which, in particular, features an optically imaging device, for example, a CCD or CMOS camera for the colors red, blue and green, as an optical detector and a white light source, may be inferred from the special practical implementation section.

One preferred application of the method according to an embodiment of the present invention is an embodiment as an in situ process control in the production of optically thin layers deposited from the vapor phase onto a substrate. In this context, the method is integrated into a control loop which is used to control the calculated actual values of the optical layer parameters of the optically thin layers as control variables to preset nominal values by adapting the production parameters as manipulated variables in accordance with the ascertained actual values for the optical layer parameters.

In addition, the method according to an embodiment of the present invention may also be used for in situ process control when no optically thin layers, but rather absorbent layers are grown. In that case, the method according to an embodiment of the present invention may at least be utilized for estimating the stoichiometry. Reflection intensity R of the diffuse or direct light scattering emanating from the layer deposited onto the substrate is interpreted accordingly outside of the total reflection in at least two wavelengths $\lambda_1$, $\lambda_2$. A distinct change in the characteristic curve indicates the point of stoichiometry reached. In addition, the method according to an embodiment of the present invention permits simultaneous monitoring of the temperature of the vaporization sources by the spatially resolved optical detection in that the occurring color values of the thermal radiation of the vaporization sources are interpreted. Finally, an application may also be carried out on rough substrates or rough, deposited layers since there is no dependency here due to the use of incoherent light. However, if the influence of the roughness is also to be taken into account, coherent (laser) light is to be used accordingly. Further details regarding the preferred applications may likewise be inferred from the detailed description section.

I) Theoretical Fundamentals of an Embodiment of the Method According to the Present Invention The starting point for developing the method according to an embodiment of the present invention resides in the wave theory. This theory describes the propagation of waves in dielectric media and is from the field of high-frequency engineering. In the case of an embodiment of the present invention, the wave theory is applied to optically thin layers. Each layer is interpreted as an individual transmission line having a parameter set composed of a propagation constant, field wave impedance and thickness (corresponds to the transmission line length) and is uniquely described (compare FIG. 1A). In the left part of FIG. 1A, two optically thin layers are represented by two wave impedances $Z_{F1}$, $Z_{F2}$ and thickness d of the growing top layer.

Field wave impedance $Z_F$ is defined as a function of the dielectric in which the wave resides. A material is able to be uniquely described by permeability $\mu$ and permittivity $\varepsilon$.

$$Z_F = \sqrt{\frac{\mu}{\varepsilon}} \quad (1)$$

Field wave impedance $Z_F$ in accordance with equation (1) is definable using the two mentioned variables. It likewise holds in accordance with another notation for field wave impedance $Z_F$ that:

$$Z_F = Z_{FO} \cdot \frac{1}{n - jK} \quad (1a)$$

Value n is the (real) refractive index, and K is the extinction coefficient (imaginary refractive index). In this case, $ZF_0$ is the wave impedance of the vacuum and is a physical constant. Thus, in the case of one single layer, two different wavelengths are already required for the system solution since two unknowns (n and K) arise.

If, at this point, another unknown layer grows on the now known layer, the following formula applies, which also takes the thickness of the layer into account. The origin of the equation is the telegraph equation (general form of the wave equation). The known layer ($Z_{F1}$; in the case of a first layer to be deposited, is then a substrate; for each additional layer, it is the layers subjacent thereto) and the growing (unknown) layer ($Z_{F2}$; always the topmost layer) are combined into a common layer ($Z_G$) that is dependent on the thickness and the complex refractive index. Thus, three different wavelengths are needed for the detection process to ascertain the three unknown variables.

Figure 1B:
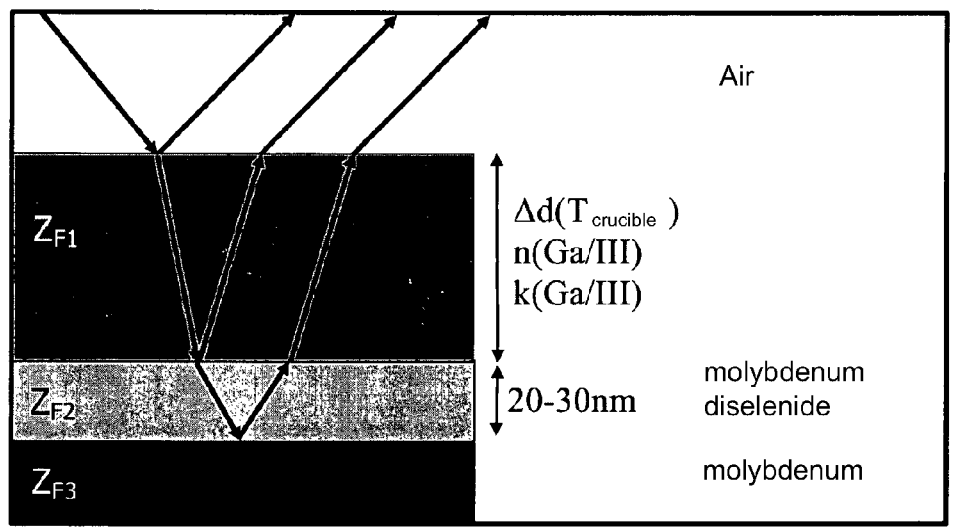
FIG. 1B is a schematic diagram illustrating interferometry on optically thin layers.

FIG. 1B illustrates the interferometry of optically thin layers having layer impedances $ZF_1$, $ZF_2$ (optically thin layers) and $ZF_3$ (substrate, in the selected exemplary embodiment, of molybdenum) relative to air. The first layer (layer thickness 20-30 nm) is composed of a compound of the vaporized selenium with the molybdenum of the substrate; the next layer is composed of a compound of gallium and selenium. Unknown are layer thickness $\Delta d$ (given a known temperature of the vaporization sources), refractive index n (real part) of gallium from third main group (Ga/III) and absorption coefficient K (imaginary part) of Ga/III.

In accordance with the field wave impedance theory, the two layers are combined to obtain a total impedance $Z_G$. It holds that:

$$Z_G = Z_{F2} \cdot \frac{Z_{F1} + Z_{F2} \cdot \tanh(\gamma \cdot d_{opt})}{Z_{F2} + Z_{F1} \cdot \tanh(\gamma \cdot d_{opt})} \quad (2)$$

Once total impedance $Z_G$ of the two layers is obtained, reflection intensity R of the incident optical radiation of the layer system may be calculated. If $Z_{F0}$ is the field wave impedance of the vacuum, it holds that:

$$R = \frac{(Z_{F0} - Z_G)^2}{(Z_{F0} + Z_G)^2} \quad (3)$$

Value $\gamma$ (propagation constant) describes the propagation of a wave and is described only by the imaginary refractive index and the wavelength used:

$$\gamma = \frac{2\pi}{\lambda} \cdot \frac{Z_{F0}}{Z_{F2}} = \frac{2\pi}{\lambda} \cdot (K + jn) = \frac{2\pi}{\lambda} n_{complex} \quad (4)$$

In a vaporization process, the calculation unit performs the calculations of equations (2) and (3) in situ in order to determine the thickness and the complex refractive index. To that end, the measurement signals of the optical detector in the three different wavelengths are numerically adapted ("fitted"

using varied values for the complex refractive index and layer thickness) to the mentioned optical layer model and to the results of formulas 2 and 3.

II) Sequence of the Calculations of the Complex Refractive Index and of the Thickness of a Layer Vapor-Deposited onto a Known Substrate.

Preliminary remarks: The method according to an embodiment of the present invention requires that three wavelengths $\lambda_1, \lambda_2, \lambda_3$ be used. The reason for this resides in the missing reference variable of the incident radiant light. The light typically arrives in the vaporization chamber via a plate that is regularly unintentionally vapor-coated as well. Thus, even knowledge of the radiation source intensity is of little value since a vapor-coated plate, through which the light is radiated, heavily influences the characteristic of the light. Therefore, in the context of an embodiment of the present invention, another reference had to be found for measuring the reflection. One of the three unknown variables (real and imaginary refractive index, as well as the thickness) should serve as a reference. However, the complex refractive index is wavelength-dependent and, therefore, may not be used. However, the thickness is not wavelength-dependent and may, therefore, be used as a reference since it must be identical for all measured wavelengths. Therefore, the method according to an embodiment of the present invention may be described as "self-referencing." The starting point for calculating the method according to an embodiment of the present invention is the measurement of the reflection intensity in three different wavelengths $\lambda_1, \lambda_2, \lambda_3$. For this, a CCD (charge-coupled device) may be used very advantageously as an optical detector. Through the use of the CCD, reflection intensity R of three wavelengths $\lambda_1, \lambda_2, \lambda_3$ (red, green and blue) is made available, thereby allowing individual analysis thereof. It should be noted in this connection that the reflection intensity is provided as a function of time. Time is converted into thickness at the beginning of the deposition process on the basis of the occurring interference maxima. The calculated thickness is optical thickness $d_{opt}$, i.e., the previously unknown refractive index is initially contained in the thickness. It holds that:

$$2 \cdot n \cdot d \cdot \cos\varphi = \left(m + \frac{1}{2}\right)\lambda \quad (5)$$

In this connection, m corresponds to the order of interference, $\varphi$ is the angle of incidence, $\lambda$ is the wavelength of the incident light. The equation is able to reproduce the conversion from the time-dependent to a thickness-dependent representation.

$$\Delta d_{opt} = d_{opt2} - d_{opt1} = \frac{[m_2(t) - m_1(t)] \cdot \lambda}{2n \cdot \cos\varphi} \quad (6)$$

Given defined conditions, optical layer thickness $d_{opt}$ is calculated as half of wavelength $\lambda_R$ of the time characteristic of the reflection intensity.

$$d_{opt} = \lambda_R/2 \quad (6a)$$

Figure 2:
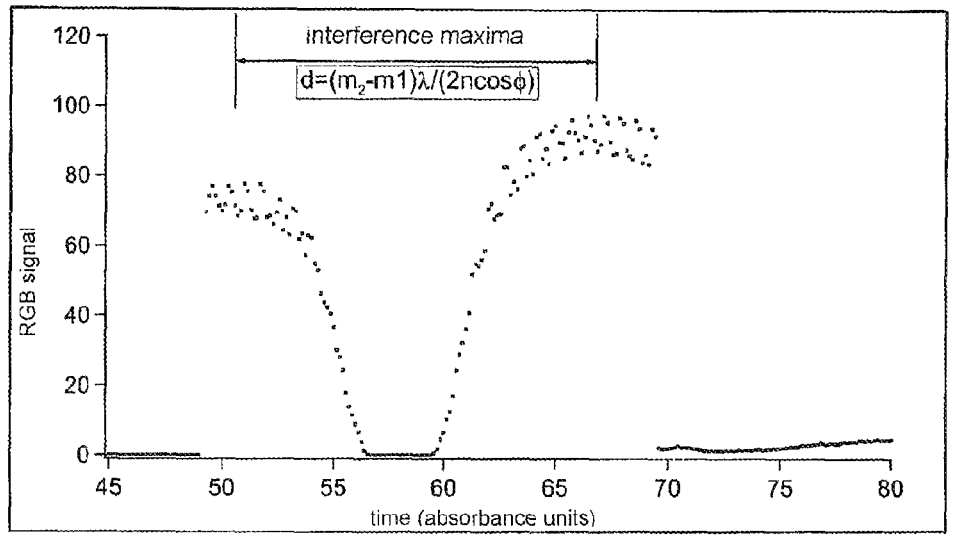
FIG. 2 is a representation of the conversion of the time dependency of the reflection intensity into the thickness dependency.

FIG. 2 shows a diagram for converting the time dependency of reflection intensity R (ordinate: RGB signal, abscissa: time in any given unit) to thickness dependency. Parameter $d_{opt}$ is calculated from the quotient of real layer thickness $d_{layer}$ and complex refractive index $n_{complex}$.

$$d_{opt} = \frac{d_{layer}}{n_{complex}} \quad (7)$$

The reflection intensity is definable using the wave impedance in accordance with equation (3). The wave impedance of vacuum $Z_{F0}$ is known and thus total impedance $Z_G$ of the vapor-deposited layer may be considered by rearranging equation 3. Impedance $Z_G$ describes the vapor-deposited layer and the subjacent substrate. To separate the two layers from one another, equation (2) is still applied taking equation (4) into account.

A fit is performed to compare equation (2) to the measured reflection intensities. In this context, the measured values are individually determined for all three measured wavelengths by fitting equation (2).

An Overview of the Calculation Steps:

I) Actual thickness d is numerically calculated for all three wavelengths, whereby the thickness of the vapor-deposited layer must have the same value for all three wavelengths.

II) Equation (2) is solved for each of the wavelengths using the calculated thickness from step 1. In this connection, the reflection measurement of each individual wavelength is fitted using equation (5) and applied equation (2). The fit is conceived in such a way that the known substrate and the known thickness are introduced into equation (2). Value $\gamma$ may be described by equation (4). Thus, a numerical equation still remains for the wave impedance of the vapor-deposited layer. This equation is fitted and, at the smallest error, the real thickness and the refractive index are determined.

III) Steps 1 and 2 are repeated for the entire process until the limit of the interferometry is reached (layer too thick or too highly absorbent).

Figure 3A:
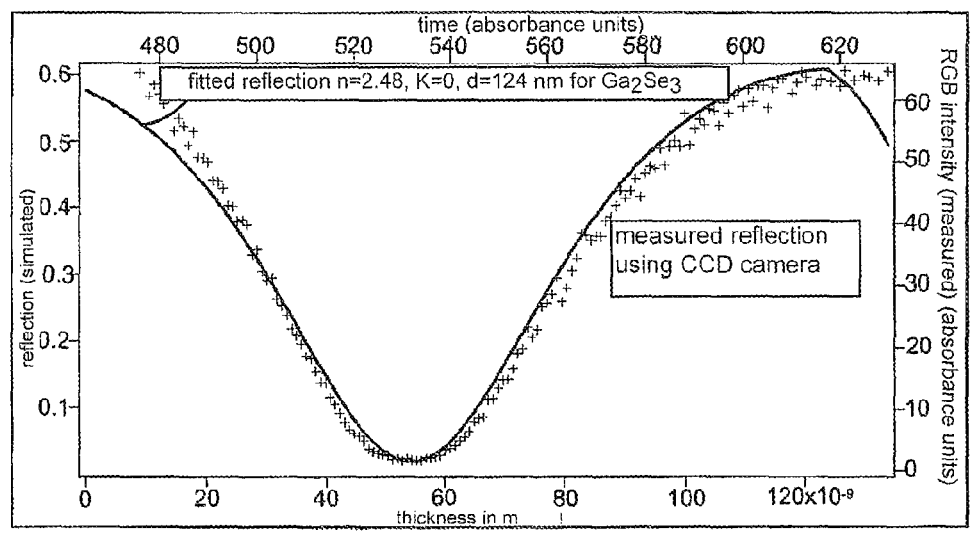
FIG. 3A . . . D are diagrams of the fitted reflection during the deposition process.
Figure 3B:
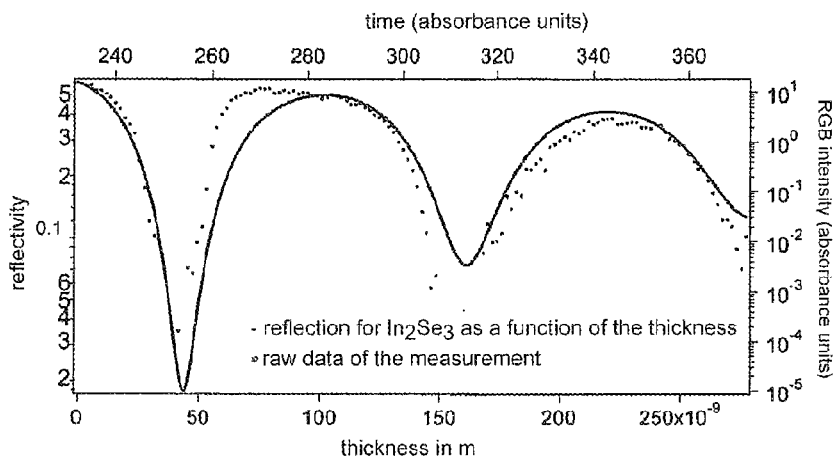
Figure 3C:
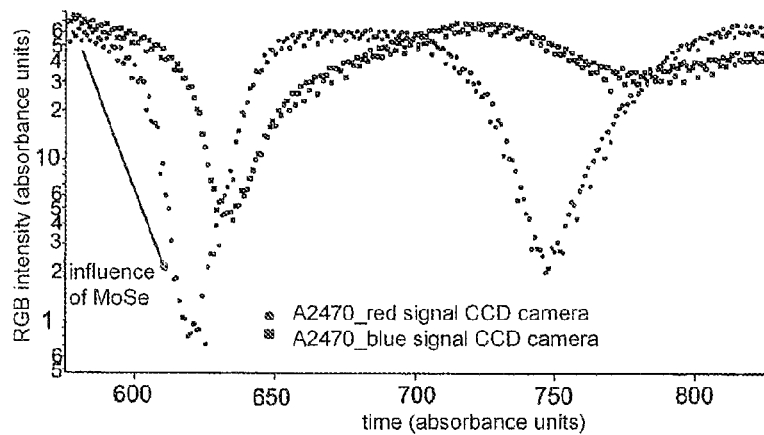
Figure 3D:
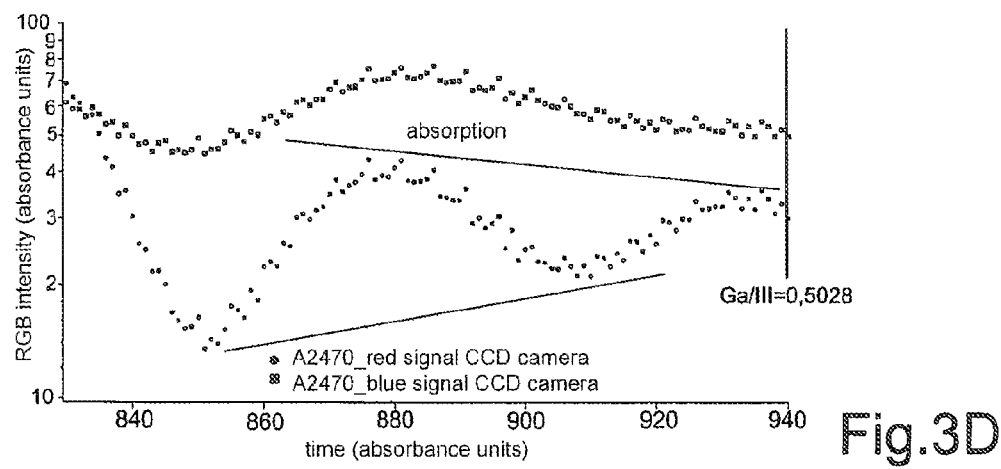

FIG. 3A shows the reflection (solid line) fitted to the measured reflection intensity values (+) of $Ga_2Se_3$ for a process in the context of the deposition (ordinate: RGB signal, abscissa: time in any given unit). FIG. 3B shows exemplarily how the method according to an embodiment of the present invention functions. The fitting (the optical layer model) is performed during the measurement and computes the thickness and the complex refractive index during the process. While the thickness is readily discernible in FIG. 3B as an axis over time, the measurement of the complex refractive index is not shown. In the case of optically thin systems, it is only possible to determine the thickness and the complex refractive index together since the two are mutually correlated. Thus, more information is needed to determine the refractive index. From the interferometry, it is known that three wavelengths suffice (thickness and complex refractive index). When working with white light, an infinite number of wavelengths are available for the measurement. FIG. 3C shows the intensity profile of the red (circles) and the blue (squares) reflections over time in the context of a simultaneous vaporization of Ga and Se onto a molybdenum foil as a substrate, while Cu and In are closed. The influence of the initially forming MoSe is denoted by an arrow. As in the case of FIG. 3B, it is again readily inferable that the optical layer thickness corresponds to half of the spacing between the two minima. At the end of this first vaporization phase in stage I, the composition of the deposited layer is precisely known from knowledge of the complex refractive index and the real layer thickness and is used as a reference for the subsequent vapor deposition of In and Se (given closed Ga and Cu) as a deposited layer. FIG. 3D shows the corresponding intensity profile of the red (circles) and the blue (squares) reflections over time in stage I. Also shown by a corresponding simulation of the enveloping curve is the absorption resulting from the deposited layer. At the end of the second vaporization phase in stage I, a Ga/III fraction of 0.5028 is obtained as the Ga concentration relative to the In+Ga (Ga/Ga+In) concentration from the calculated optical layer parameters. Thus, the composition of this layer is known for the subsequent processes and may be considered accordingly.

Figure 4:
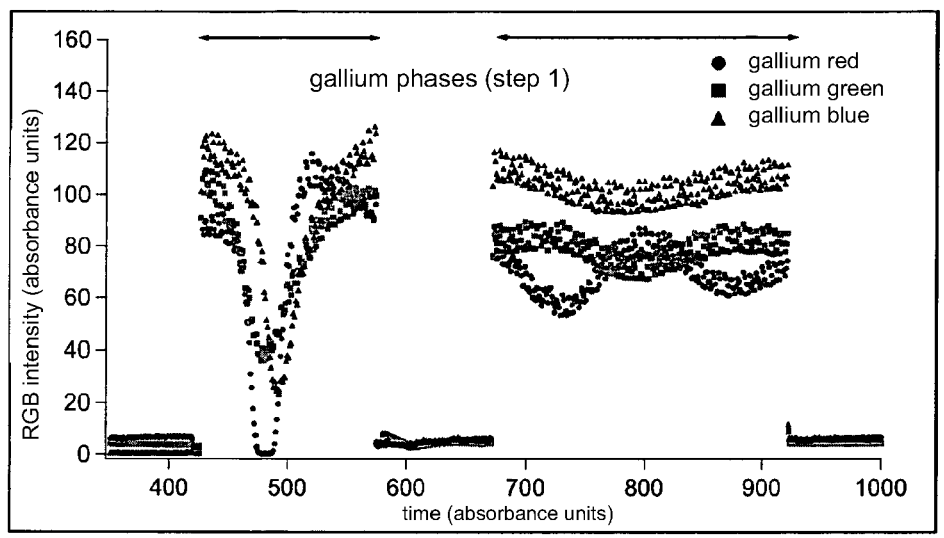
FIG. 4 is a diagram for representing the measurement signals of all three color components of an image signal.

The routine shown is carried out for all three wavelengths. For the phase of a vaporization of gallium and selenium (stage I, sequential vaporization of gallium (given zero concentration of gallium, indium is vaporized, continuous vaporization of selenium), FIG. 4 shows all three analyzed wavelengths simultaneously (ordinate: RGB signal, abscissa: time in any given unit). The triangles indicate the analysis of the blue wavelength, the squares the analysis of the green wavelengths, and the circles the analysis of the red wavelength.

III) Application of the Calculations to a Specific Exemplary Embodiment.

Figure 5:
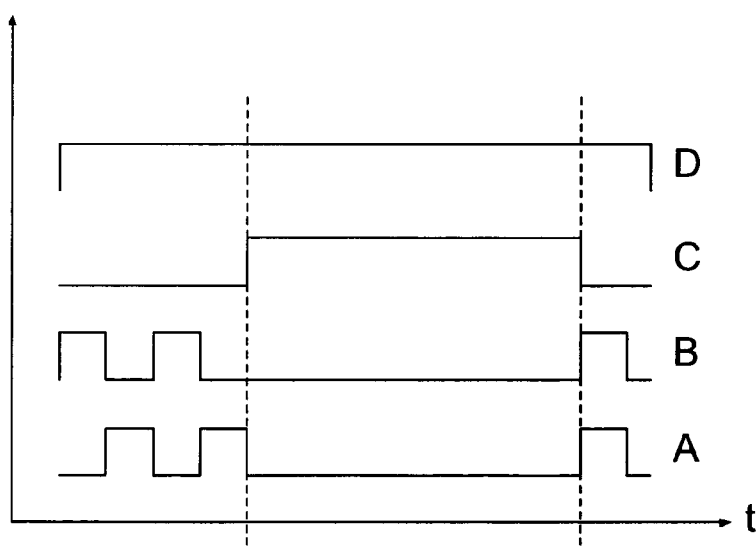
FIG. 5 is a process diagram of an entire PVD process.
Figure 6:
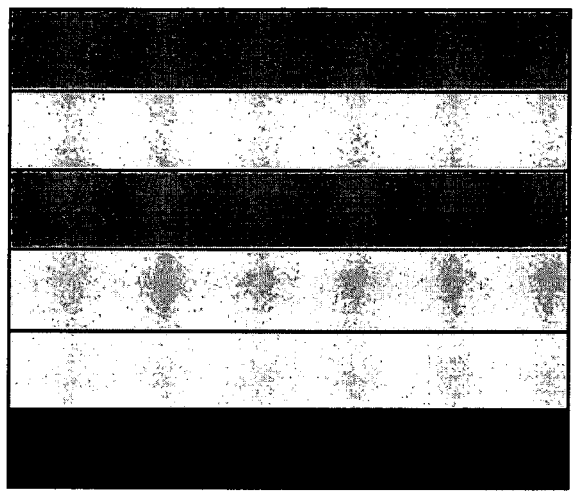
FIG. 6 illustrates a stack of deposited optically thin layers for the entire PVD process.
Figure 7:
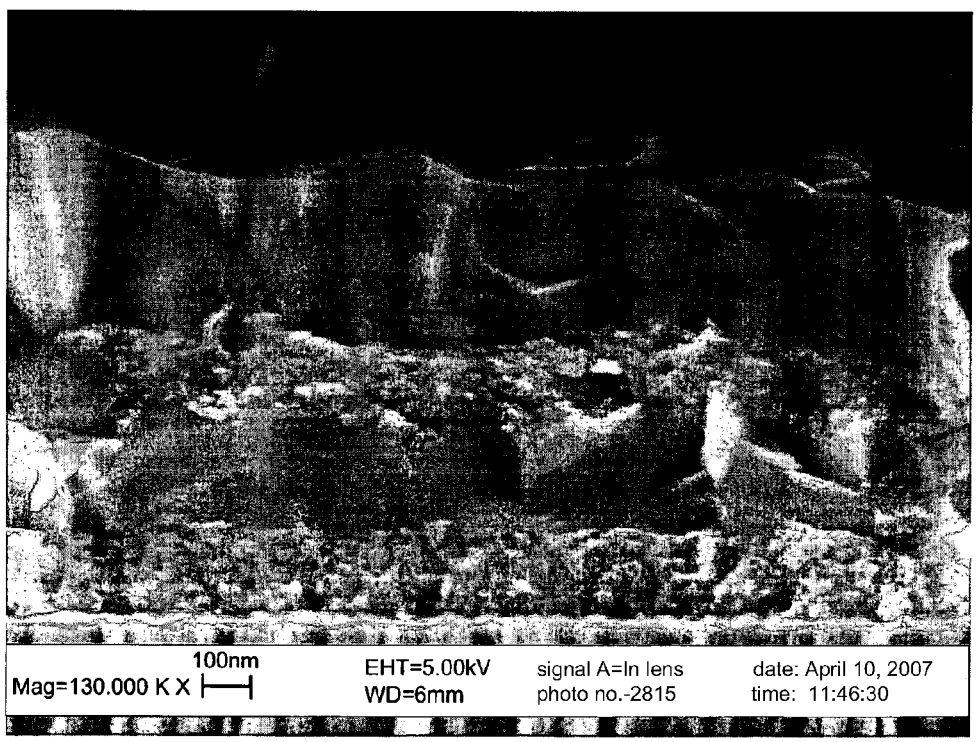
FIG. 7 is a Raster Electron Microscope (REM) photograph of a stack of a plurality of layers.

The exemplary embodiment of the method according to the present invention relates to the sequential co-vaporization of metals and non-metallic elements of the V. to VII. main group, there being at least one sequence of the vaporization. One possible time sequence for the vaporization of elements A (for example, In), B (for example, Ga), C (for example, Cu) and D (for example, Se) may be inferred from FIG. 5. The process described here is a sequential co-vaporization of the type Ga+Se, followed by In+Se, to obtain a layer stack of $Ga_2Se_3$ and $In_2Se_3$. The stack of optically thin layers that is able to be produced by this vaporization process in stage I is schematically illustrated in FIG. 6. A high-resolution REM photograph of a complex stack of a plurality of optically thin layers that are layered one over the other is shown in FIG. 7. By employing the method according to an embodiment of the present invention, the topmost deposited layer may always be analyzed as a reference layer in terms of its material composition, in relation to the subjacent layers. Therefore, the method is also applicable to stacks having any desired number of individual layers. In stage II of the process mentioned above, an absorbent Cu-containing layer is produced for which interferometry is not applicable. In this case, however, the method according to an embodiment of the present invention may be utilized for estimating the stoichiometry. In stage III, analyzable optically thin layers are then deposited again.

Figure 8:
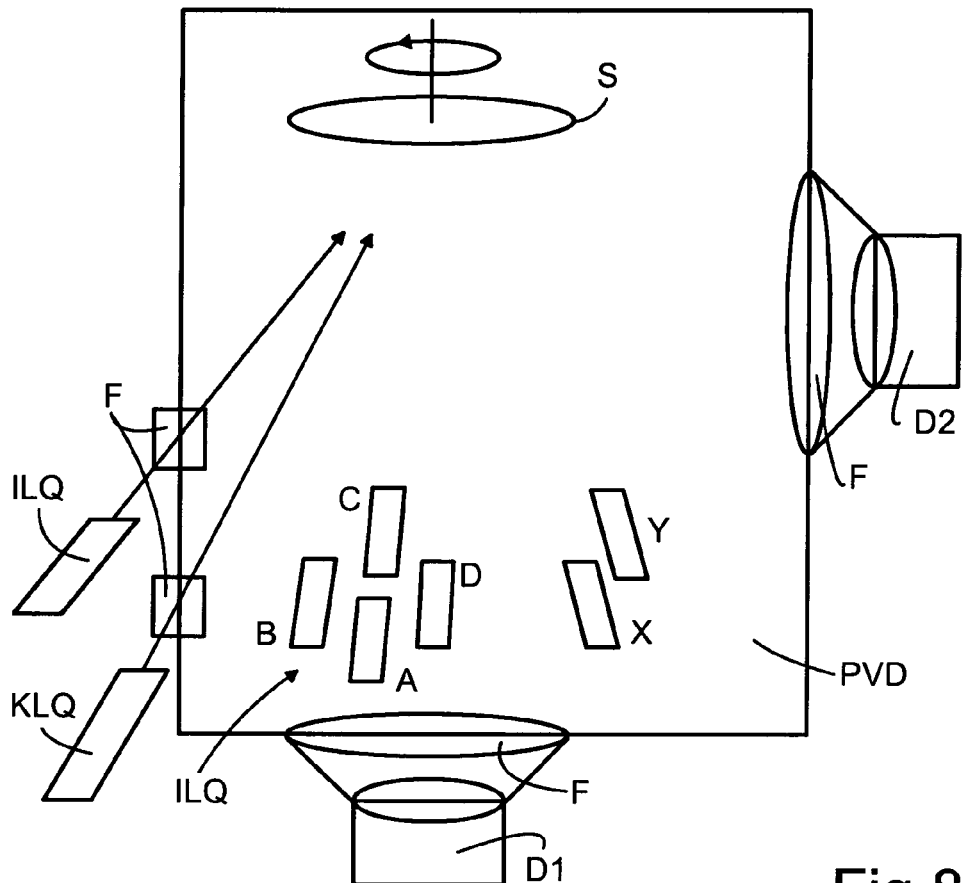
FIG. 8 is a diagram for an system for an entire PVD process.

The basic design of an arrangement for implementing the method according to an embodiment of the present invention is shown in FIG. 8. In a PVD chamber PVD, elements A, B, C, D are sequentially vaporized and are deposited as composite layers on the deposition side of substrate S which is rotating in the exemplary embodiment. In this context, as a function of their composition, the layers being deposited reflect incident radiant light as diffuse or direct reflections of incoherent radiation (no total reflection). During the entire deposition process, the diffuse or direct reflections are recorded by at least one spatially resolving optical detector D1. Another detector D2 may be provided orthogonally to first detector D1, for example, laterally with respect to substrate S. The optical radiation interacts with the vapor-deposited optically thin layer in a characteristic manner, so that the quality of the vapor-deposited layer in terms of its composition is directly assessable from the reflection using detectors D1, D2, and, in the case of deficiencies of any kind, the control loop is able to execute a correction of the process. In the selected exemplary embodiment, vaporization sources A, B, C, D, X, Y are simultaneously used as incoherent light sources ILS in order to radiate light of different wavelengths onto the deposition side of substrate S. Alternatively or additionally, white light sources ILQ (without vaporizer function) having an infinite spectrum of wavelengths may also be used. In addition, a coherent light source KLQ (in this case, a laser) may be provided to take into account the influence of the surface roughness of the layers being deposited. Other vaporization sources X, Y may likewise be provided, for example, for vaporizing non-metallic elements.

Controlling the co-vaporization does not require any spatial separation of the individual vaporization sequences; however, it also does not preclude such a separation. Essential for controlling the vapor deposition process are the reflection measurement and the analysis of the optical radiation that is incident on the moving substrate. To that end, the radiation components must be spatially separated from one another to permit analysis of the individual radiation components in the system. For this purpose, spatially resolving optical detector D, for example, a CCD camera equipped with optical instruments, is mounted within or outside of PVD chamber PVD. In the case of a mounting outside of PVD chamber PVD, a corresponding window F is provided in the chamber wall that is likewise coated during the vaporization process with a deposition layer, so that an external referencing of the control system is not possible. This is also not necessary in the case of the method according to an embodiment of the present invention due to its self-referencing capability. Using an array of optical sensors, the CCD cameras convert received optical radiation in the wavelength region of 400 nm to 700 nm into color values. These correspond then to the incident wavelength and are calculated based on the spectral sensitivity of the individual sensors of the CCD chip. A CCD camera is composed of an array of optical sensors which allows it to locally separate the incident signals. The type of optical radiation is not limited by the use of CCD cameras. Rather, any optical radiation in the visible spectrum may be thereby used for monitoring. Furthermore, any given number and any given location of the CCD cameras are possible and may be freely selected based on the quality of the cameras that are used. The general control of moving or stationary substrates in connection with a spatially resolved optical detection is likewise achieved in a particularly elegant fashion by a CCD camera which is oriented with its optics in the direction of the substrate.

Figure 9:
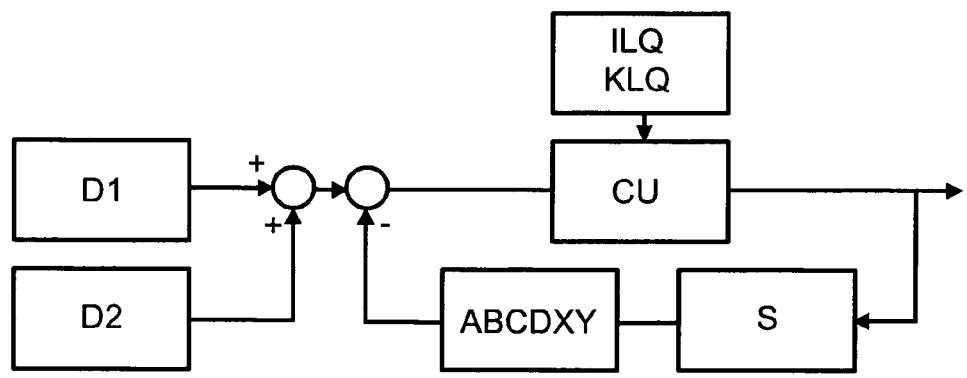
FIG. 9 is a control loop used for process control.
Figure 10:
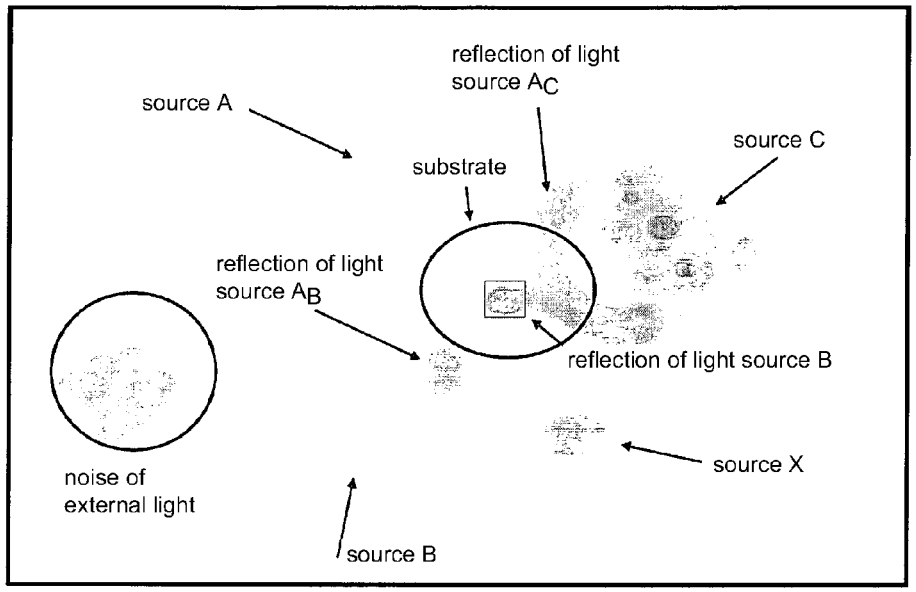
FIG. 10 illustrates measurement signals of a CCD detector (stage I)

The method according to an embodiment of the present invention may preferably be used as a process control for a vaporization process of the type elucidated above. Once the optical layer parameters are numerically ascertained, the process is able to be controlled by influencing the process parameters. This control thereby differs significantly from the known controls in this field where only a qualitative control (in accordance with predefined characteristic points) is possible without a precise numerical knowledge of the optical layer parameters. The function of the corresponding control loop is schematically indicated in FIG. 9 for the general case (compare FIG. 8). Detectors D1 and D2 are used for measuring the reflection intensities. They transmit the measurement signal to control unit CU. Control unit CU utilizes the measurement signals using the type of light sources (ILQ, KLQ) used for the control. In this case, the operation of the light sources is freely selectable. It may be a question of chopped or unchopped light signals. The control unit controls the movement of substrate S, as well as vaporization sources A, B, C, D, X, Y (X, Y may be non-metallic vaporization sources, for example) on the basis of the measurement signals, while correlating the same to the light sources used. Following the change in material sources (change in the vaporization rate) or in the substrate (change in the traversing velocity) that may become necessary, control unit CU again utilizes the incoming measurement signals and, in this manner, controls the vaporization process continuously and in situ. FIG. 10 shows exemplarily the measurement signal of an optical CCD detector, including visible reflections of the light sources, as well as the temperatures of the vaporization sources for stage 1 of the exemplarily selected 3-stage vapor deposition process of $Cu(In,Ga)Se_2$ thin layers. For this measurement signal acquisition, the CCD camera is located at the bottom of the PVD chamber and is oriented with its optics perpendicularly in the direction of substrate S (compare FIG. 8).

Denoted in detail in FIG. 10 are:

| | |
|---|---|
| reflection of light source $A_A, A_B, A_C, A_D$ | optical reflection of the vaporization sources on portions of the PVD chamber, respectively on the substrate/layer (shown here exemplarily $A_B, A_C$) |
| reflection of light source B | optical reflection of a light source |
| source A, B, C, D, X, Y | vaporization sources (shown here exemplarily: A, B, C, X) source A: 935° C., source B: 910° C., source C: 1,300° C. |
| noise of external light | stray light which is recorded by the CCD camera spatially separately and is thereby filtered and becomes negligible |
| substrate | schematic position of the substrate within FIG. 10 |

Besides its use for the spatially resolved measurement of different light sources, a CCD camera also allows the function of the vaporization sources to be monitored by estimating the temperature thereof via control unit CU. In the grayscale representation in FIG. 10, the colors of the original measurement report are reproduced only by their grayscale values. The original measurement report reveals a red reflection of light sources $A_C$ and B, a green reflection of light sources $A_B$ and of vaporization source B and X, as well as in the case of external noise, and a blue reflection in the case of vaporizer source A and C (with red islands). While vaporization sources A and B exhibit approximately the same temperature and, therefore, a similar temperature radiation, temperature distribution and temperature color, vaporization source C is operated at a significantly higher temperature. The CCD camera displays the higher temperature as a blue color. In the case of a faulty function, the vaporization source is not able to take on a blue coloration, instead it would not be visible. Due to the high temperature, vaporization source C has intensity points which, due to the other colors, are measured as blue within the temperature distribution. The CCD camera is adapted to the human eye, whereby highest intensity regions are displayed as the color green since the human eye has its highest sensitivity for green.

The reflections of the individual light sources (also vaporization sources) are represented in FIG. 10. When used as measurement signals for a control loop, the measurement signals must initially be analyzed by control unit CU for semi-transparent, optically thin layers. The CCD camera locally separates the reflections from one another and thereby renders possible a separate analysis within the control unit. The control unit subsequently converts the measured, separate reflection intensities of the individual light sources into numerical intensities and plots them in a curve as a function of time.

Figure 11:
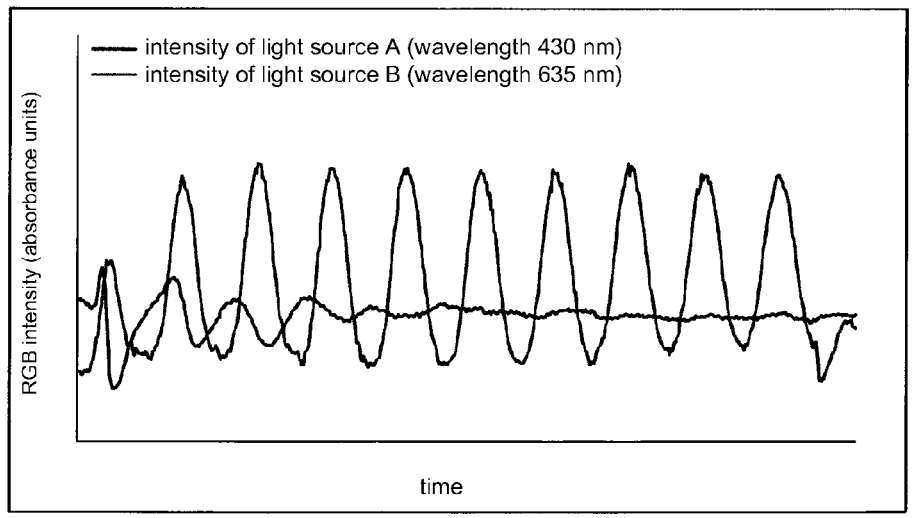
FIG. 11 is a diagram of the intensity profile of the reflections over time (stage I)

FIG. 11 shows the time characteristic of the locally separated reflection intensities at the substrate surface processed by the control unit (red-green-blue intensity "RGB intensity" in any given absorbance unit (a.u.) over time). The wavelengths of light sources A and B are indicated by their wavelength. In the exemplary vaporization system used, a laser module is used as light source B. Light source A is attributable to the temperature radiation of source A (in this case: molten gallium). From the physical laws that are reasonably well known for determining an optically thin layer, the thickness of the layer that is formed, as well as the complex refractive index (two components) of the deposited layer (see above) may be determined on the basis of two different wavelengths. In addition, there is a discernible difference in FIG. 11 between the characteristics of the short-wave temperature radiation of source A and the long-wave radiation of light source B. The intensity of this radiation decreases visibly. In this manner, the control unit may ascertain that the deposited substance absorbs the blue radiation. In contrast, the red radiation is not absorbed, as is made visible by an only slight decrease in the interference signal. The control unit contains data pertaining to the layer to be expected on the substrate and, based on this data, which is present in the form of step diagrams and values for the wavelength-dependent complex refractive index, determines the optical layer parameters and, as a function thereof, the layer composition of the substance formed. In the illustrated example in accordance with FIG. 11, the control unit provides the information that the deposited layer is $Ga_2Se_3$. This substance has a refractive index of 2.4 and first absorbs at a wavelength of below 580 nm.

The method according to an embodiment of the present invention is only limited by the thickness of the deposited layer since, at or above a thickness of approximately ten times the wavelength of the incident radiation, the interferometry no longer yields valid results. However, since an embodiment of the present invention is limited to optically thin layers, this limitation is not reached and is thus negligible. For optically thin layers, in one specific embodiment in accordance with FIG. 8, the method according to an embodiment of the present invention provides an adequate control possibility for the interferometric calculations and thus may be used for the purpose of a process control. Nevertheless, by employing the method according to an embodiment of the present invention, at least one stoichiometric estimation may be performed for absorbent layers due to the special optical analysis. Such an estimation is also described, for example, in German Examined Specification DE 102 56 909 B3.

Figure 12:
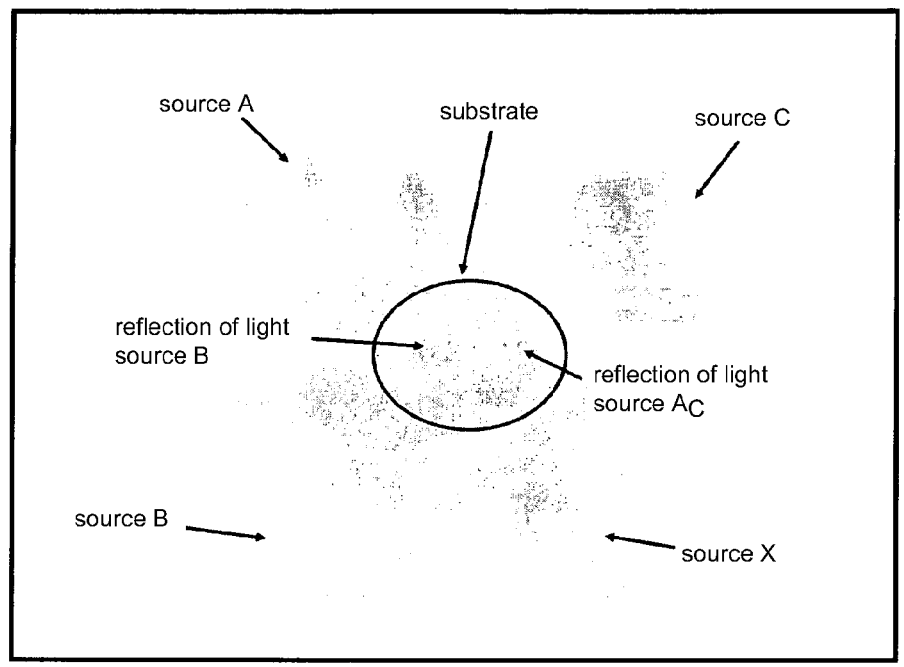
FIG. 12 illustrates measurement signals of a CCD detector (stage II)

The procedure is explained based on the example of the vapor deposition of a $CuInGaSe_2$ layer. In stage I, a semitransparent layer of indium, gallium and selenium are deposited on the substrate. FIG. 12 shows the measurement signal of the CCD camera for the vaporization of copper in stage II onto the just described semitransparent layer. An exemplary measurement signal of the detector, including visible reflections of the light sources, as well as the temperatures of the vaporization sources for stage II are shown.

Denoted in detail in FIG. 12 are:

| | |
|---|---|
| reflection of light source AC | optical reflection of the molten copper on the substrate |
| reflection of light source B | optical reflection of a light source on the substrate |
| source A, B, C, D, X, Y | vaporization sources (shown here exemplarily: A, B, C, X) source A: 935° C., source B: 910° C., source C: 1,300° C. |
| substrate | schematic position of the substrate within FIG. 12 |

FIG. 12 shows the recorded area of the CCD camera which is used for controlling the process. In comparison to FIG. 10, here the interference signal of an external radiation has been cut out by spatially resolving the measurement signal. During this exemplary process, the rotation induces a partial covering of the two light sources A and B. However, due to the processing of continuous measurement signals, the control unit is able to separate both reflections and analyze them individually. The mentioned reflection of light source B corresponds to the already described exemplary light source for estimating the temperature of the vaporization sources in order to verify functioning.

The goal in this exemplary process is estimating the stochiometry in the amount of substance from the metals indium and gallium and the metal copper. For a stoichiometric Cu(In, Ga)Se$_2$ thin layer, the quantities of indium and gallium should correspond to the quantity of copper on the substrate. The control unit is calibrated on the basis of the target composition for this substance and may thereby perform the estimation for the stoichiometry. In this specific example, the CCD camera measures the process until the processed measurement signals in the control unit detect the formation of a copper selenide (Cu$_{2-X}$Se) coating on the surface of the deposited layer. For a CCD camera, this effect is visible due to the continuous increase in the intensity of the reflection of light source A$_c$, accompanied by a simultaneous decrease in the reflected intensity of light source B in the exemplary system.

Figure 13:
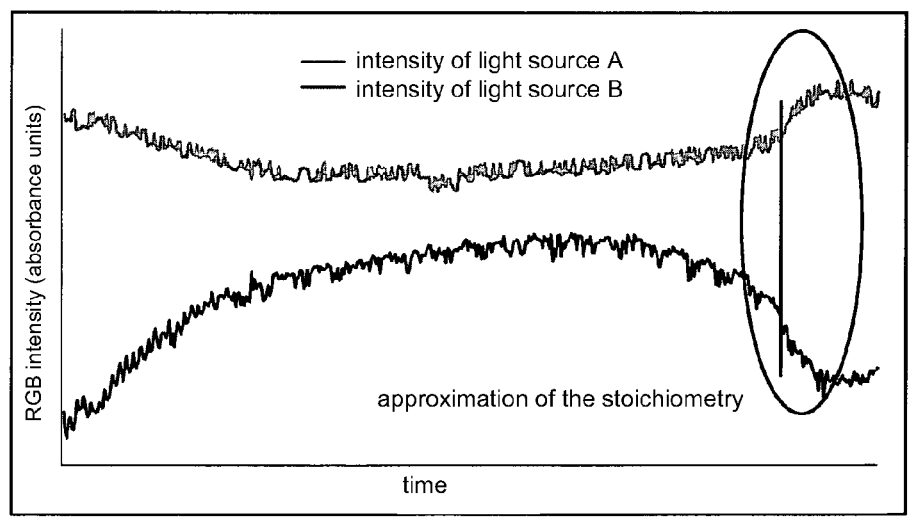
FIG. 13 is a diagram of the intensity profile of the reflections over time (stage II)

FIG. 13 shows the time characteristic of the measurement of the CCD camera (red-green-blue intensity "RGB intensity" in any given absorbance unit (a.u.) over time) that is analyzed by the control unit. The characteristic curve of the temperature reflection of the copper source (top curve, color green, "intensity from light source A") is shown together with the reflection of light source B (in this case: laser of wavelength 635 nm, lower curve, color red, intensity from light source B"). The described properties are clearly indicated in FIG. 13 by the oval ("approximation of stoichiometry"). The occurrence of these properties satisfies the requirement for estimating the stochiometry within the deposited layer.

Figure 14:
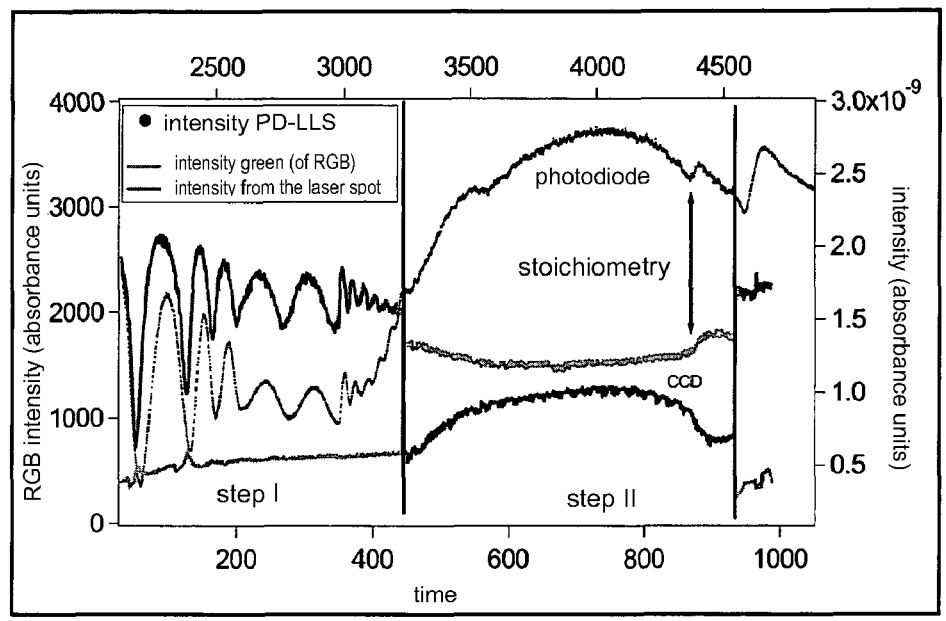
FIG. 14 illustrates a comparison of the measurement signals according to an embodiment of the present invention/according to the related art.

To control the method according to an embodiment of the present invention for measuring optical reflections, analyses of the control unit are compared to those of the control system in accordance with the German Examined Specification DE 102 56 909 B3. In this control system, a photodiode is used along with a subsequent lock-in amplifier. The photodiode receives a modulated reflected signal from the substrate surface, integrates the entire signal and extracts the modulated signal for analysis. Thus, no spatial resolution of the various signals is provided. Nevertheless, as already mentioned, a qualitative control based on characteristic individual points is possible using the method in accordance with the German Examined Specification DE 102 56 909 B3. FIG. 14 shows a comparison of the two methods as a function of the time history of the entire control process in accordance with an embodiment of the present invention (red-green-blue intensity "RGB intensity" in any given absorbance unit (a.u.) over time), the characteristic curve of the method in accordance with the German Examined Specification DE 102 56 909 B3 being additionally indicated. The lower, light gray curve in stage I shows the time history of the reflection intensity of the color green (from the RGB signal), and the upper, thick black curve shows the time history of the reflection intensity of a laser spot (color red) in accordance with an embodiment of the present invention. In comparison, the middle, thin black curve shows the characteristic signal curve from the method according to the German Examined Specification DE 102 56 909 B3. In stage I, a very similar result is discernible in the case of the measurements (compare the upper two curves); the lower curve for the method according to an embodiment of the present invention shows the general insensitivity of the laser signal during stage I given a relatively smooth substrate/layer. However, the measurement in accordance with the German Examined Specification DE 102 56 909 B3 is highly error-prone since the presence of rough layers must be assumed in the process. In this context, one problem is that laser signals, i.e., coherent radiation, are more heavily influenced by the roughness of the surface than is incoherent radiation.

It is not possible to quantitatively control the layer deposition using the method in accordance with the German Examined Specification DE 102 56 909 B3 since the roughness of the vapor-deposited layer is superimposed on the measured interferences. Since this dependency does not occur in the method according to an embodiment of the present invention due to the fact that incoherent light may be used, by employing the CCD camera, the corresponding control system makes it possible to characterize the deposited layer by numerically determining the thickness and ascertaining the refractive index. Using both systems, a unique occurrence of stoichiometry is to be observed for stage II. However, it is represented differently. For stage III, which is not shown further in FIG. 14, a quantitative analysis of the layer composition may be prepared, in turn, using the method according to an embodiment of the present invention. Typically, however, this is not necessary since, in stage III, it is only a question of exiting stage II in any case in the area of a copper-rich deposition.

Figure 15:
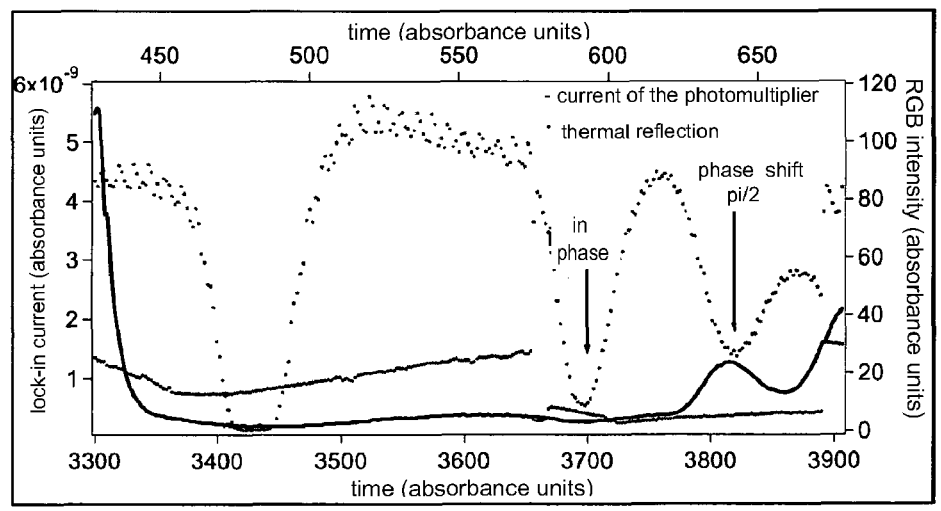
FIG. 15 illustrates a a comparison of measurement signals on rough layers between coherent and incoherent light sources.

FIG. 15 shows a comparison of coherent and incoherent light sources on rough substrates. A simultaneous measurement is illustrated between the method according to an embodiment of the present invention and the method according to the German Examined Specification DE 102 56 909 B3 (LLS). In the diagram, the process has begun, and the first gallium layer and the first subsequent indium layer are applied. The measurement signal of the LLS (curve c) shows a very weak signal, while the signals of the method according to an embodiment of the present invention are clearly discernible. In the first indium phase, the influence of the roughness on the laser signal is again clearly indicated by arrows. An apparent phase shift of the reflection signals of the LLS does not permit a precise measurement, whereas the method according to an embodiment of the invention employing white light sources does not show any phase shift.

IV) Overview of the Possible Variations of the Method, as Well as of the Process Device, and of the Uses in Accordance with an Embodiment of the Present Invention I. The known vaporization sources A, B, C, D, X, Y are vaporization sources for any given elements—A, B, C, D: any given metals, X, Y: any given non-metallic elements of the V. to VII. main group.

II. The known light sources A, B are light sources of any given kind
a.) coherent sources, lasers of any given kind (for example, gas-discharge lasers, laser diodes and other sources of coherent, optical radiation)
b.) monochromatic, non-coherent light (for example, light-emitting diodes of any given optical wavelength, separation of continuous optical spectra using optical methods, for example, monochromators, filters)
c.) non-monochromatic, non-coherent light (for example, white light sources, such as halogen lamps, gas-discharge lamps; in addition, white light-emitting diodes or batteries for producing optical radiation)
d.) other light sources (for example, optical radiation of molten metal, of the melts produced in sources A, B, C, D, as well as optical radiation of melts of the described sources X, Y).

III. Known light sources A, B may be positioned
  a.) within the process device at any given angle α
  b.) outside of the process device at any given angle α using heated or unheated, optically transparent devices (for example, windows)
IV. The radiation of known light sources A, B may be coupled in by
  a.) direct illumination of the substrate during the vapor deposition process to be controlled by light sources known according to II., without optical instruments
  b.) direct illumination of the substrate during the vapor deposition process to be controlled using light sources known according to II. having any given upstream optical instruments (for example, linear and circular polarizers, convex and concave lenses for imaging, interference filters or other filters for adjusting the wavelengths of the light sources)
  c.) direct illumination of the substrate during the vapor deposition process to be controlled using light sources known according to II. by guiding the optical radiation using optical fibers (for example, optical monomode and multimode fibers, mirror systems for deflecting the optical radiation and for adjusting the position and the angle of incidence on the substrate)
V. The known detectors are spatially resolving optical sensors of any type of design.
  a.) integrating, spatially resolving detectors without optical instruments (for example, photodiode rows or arrays, linear array and line CCDs, which are suited for measuring optical radiation, arrays of a plurality of spatially separate photodiodes)
  b.) integrating, spatially resolving detectors having optical instruments (for example, known elements in accordance with V.a.) including imaging convex or concave lenses, interference filters or other filters for adjusting the sensitivity to specific wavelengths, dispersion of optical signals using monochromatic prisms or filters)
  c.) non-integrating, spatially resolving detectors without optical instruments (for example, CCD cameras of any given variable resolution and design, photoplates, light-sensitive papers (films), camera systems for imaging)
  d.) non-integrating, spatially resolving detectors having optical instruments in accordance with V.c.) (for example, cameras having imaging optical devices— concave and convex lens systems, compound lenses for digital and analog cameras used in image acquisition)
VI. The known substrate is of any given kind (for example, metal foils, glass sheets, plastic films; the substrates are optionally coated with current-conducting materials, such as molybdenum and suitable materials, such as sodium fluoride, for promoting the layer formation)
VII. The motion of the mentioned substrate is of any type (for example, rotation, linear motion in the vertical and horizontal direction and any combination of the two previously mentioned motions, including substrate at standstill).
VIII. The layer to be deposited during the vaporization process is of any kind and may be used to
  a.) produce an absorber layer for use in photovoltaic applications (for example, in thin-layer solar cells of the structure $ABCXY_2$, such as $Cu(In_xGa_{1-x})(S_ySe_{1-y})_2$, as well as of the structure $A_2(BC)_xD_{1-x}(X_yY_{1-y})_4$, such as $Cu_2(ZnSn)_xGa_{1-x}(S_ySe_{1-y})_4$ having any given values for x, y between 0 and 1)
  b.) produce precursor layers of binary and ternary compounds for producing the absorber layers described in VII.a.) of the type ABXY (for example, InS, GaS, InSe, GaSe as an example of various possible compositions)
  c.) produce any given binary, ternary and quaternary layers, also used for purposes other than photovoltaic applications.
  d.) produce absorbent semiconductor layers from the precursor layers described in VIII.b.) by reactive processes during the vaporization of X or Y (for example, selenization and sulphurization of precursor layers)
  e.) produce other layer systems not mentioned in VIII. a.)-d.) which are able to be controlled using the method according to an embodiment of the present invention;
IX. The system for using the control system is of any type and may be used for
  a.) controlling a sequential single- or multi-stage system which, per sequence, vaporizes at least one metal and one non-metal in accordance with I. to produce optically thin layers in accordance with VIII. (for example, physical vapor deposition—PVD);
  b.) controlling a thermal process which implements the method in accordance with VIII.d.);
X. The control unit of the control system according to an embodiment of the present invention makes use of the digital and analog inputting of imaging and integrating methods using instruments in accordance with V.; processing of input measurement signals using digital technologies (for example, computers) and controlling signals are transmitted by the control unit using digital technologies to the systems to be controlled in accordance with I, VII. The following take place:
  a.) analysis of the measurement signals using detectors in accordance with V.;
  b.) controlling the temperature of the sources in accordance with I., of the substrate in accordance with VI., and of the movement of the substrate in accordance with VII. (for example, temperature change or covering of the sources in accordance with I); and
  c.) correlation of external measurements of all relevant systems using the control system for checking and calibration (for example, performance and temperature measurements of the sources according to I., velocity measurement of the substrate according to VI. and VII.)
XI. The use of the control unit is of any type and suited for
  a.) the in situ controlling of continuous processes according to IX for producing optically thin layers according to VIII; and
  b.) the in situ controlling of sequential processes according to IX for producing optically thin layers according to VIII.

While the invention has been particularly shown and described with reference to preferred embodiments thereof, it will be understood by those skilled in the art that various changes in form and details may be made therein without departing from the spirit and scope of the invention.

FORMULA AND REFERENCE NUMERAL LIST

| | |
|---|---|
| A, B, C, D, X, Y | elements/vaporization sources/light sources |
| $A_A, A_B, A_C$ | vaporization sources as light sources |
| CCD | charge coupled device (spatially resolving optical detector) |
| CU | control unit |
| D | spatially resolving optical detector |
| $d_{opt}$ | optical thickness |
| $d_{layer}$ | real layer thickness |
| F | window |
| $\gamma$ | propagation constant |
| ILQ | incoherent light source |
| KLQ | coherent light source |
| $K_{layer}$ | extinction coefficient (imaginary part - complex refractive index) |
| $\lambda$ | wavelength |
| LLS | laser light scattering |
| m | order of interference |
| $n_{complex}$ | complex refractive index |
| $n_{layer}$ | refractive index (real part - complex refractive index) |
| PVD | PVD chamber |
| $\phi$ | angle of incidence |
| R | reflection intensity |
| RGB | red-green-blue signal |
| S | substrate |
| SLS | spectroscopic light scattering |
| $Z_F$ | wave impedance of an optically thin layer |
| $Z_{FO}$ | wave impedance of the vacuum |
| $Z_G$ | total wave impedance |

The invention claimed is:

1. A method for in situ determination of a material composition of optically thin layers that are deposited from a vapor phase onto a substrate, there being an interferometrically analyzable correlation among optical layer parameters, the optical layer parameters including a wavelength-independent real layer thickness and a complex refractive index having as a real part a refractive index and as an imaginary part an absorption coefficient, the method comprising:
    irradiating the substrate on a deposition side with incoherent light of at least three different wavelengths in a visible optical region during a deposition process;
    optically detecting in a spatially resolved manner a reflection intensity of a diffuse or a direct light scattering emanating from a deposited layer outside of a total reflection in the at least three different wavelengths;
    concurrently with the optically detecting, providing numerical values of the detected reflection intensity to an optical layer model based on a general line transmission theory in which the deposited layer is interpreted as being an electromagnetic conductor having a variable field wave impedance, a propagation constant and the wavelength-independent real layer thickness that is equivalent to the conductor length;
    ascertaining values for the optical layer parameters of the deposited layer front the optical layer model for the at least three different wavelengths by numerically adapting the optical layer model to a time characteristic of the detected reflection intensities, the wavelength-independent real layer thickness being used as a reference value; and
    quantitatively determining a material composition of the deposited layer front the ascertained values of the optical layer parameters by comparing the ascertained values to standard values for optical layer parameters of known material compositions.

2. The method as recited in claim 1, wherein an optical layer thickness of the deposited layer is ascertained as half of a spacing of an interference maxima of the detected reflection intensity of the at least three different wavelengths, and wherein the product of the optical layer thickness and the complex refractive index yields the wavelength-independent real layer thickness.

3. The method as recited in claim 1, wherein a relationship between the detected reflection intensity and a total field wave impedance for each of the at least three wavelengths is in accordance with:

$$R = \frac{(Z_{F0} - Z_G)^2}{(Z_{F0} + Z_G)^2},$$

where R is the detected reflection intensity;
$Z_{F0}$ is a field wave impedance of a vacuum; and
$Z_G$ is the total field wave impedance.

4. The method as recited in claim 2, wherein a total field wave impedance of a first layer and a second layer that are stacked one on top of the other for each of the at least three wavelengths is in accordance with:

$$Z_G = Z_{F2} \cdot \frac{Z_{F1} + Z_{F2} \cdot \tanh(\gamma \cdot d_{opt})}{Z_{F2} + Z_{F1} \cdot \tanh(\gamma \cdot d_{opt})}$$

where
$Z_G$ is the total field wave impedance;
$Z_{F1}$ is a field wave impedance of the first layer;
$Z_{F2}$ is a field wave impedance of the second layer;
$d_{opt}$ is the ascertained optical layer thickness;

$$\text{constant} = \frac{2\pi}{\lambda} \cdot \frac{Z_{F0}}{Z_{F2}} = \frac{2\pi}{\lambda} n_{complex};$$

$Z_{F0}$ is a field wave impedance of a vacuum;
$n_{complex}$ is the complex refractive index; and
$\lambda$ is the wavelength.

5. The method as recited in claim 1 further comprising storing the ascertained values of the optical layer parameters of a layer and using the stored values as reference values for a next layer in the case of a layer change.

6. The method as recited in claim 1, further comprising analyzing a reflection intensity resulting from coherent light of one wavelength so as to account for the surface roughness of the deposited layer.

7. The method as recited in claim 1, further comprising:
    depositing the optically thin layers from the vapor phase onto the substrate; and
    controlling, in a control loop, calculated actual values of the optical layer parameters of the optically thin layers as control variables to preset nominal values by adapting production parameters as manipulated variables.

8. The method as recited in claim 7, further comprising depositing an optically thick layer onto the substrate,
    wherein a stochiometry of the optically thick layer is estimated by interpreting a reflection intensity of a diffuse light scattering emanating from the optically thick layer deposited onto the substrate outside of a total reflection in at least two wavelengths.

9. The method as recited in claim 7, further comprising simultaneously monitoring the temperature of a plurality of vaporization sources by at least one spatially resolved optical detector.

10. The method as recited in claim 7, wherein the substrate is rough.

11. The method as recited in claim 7, wherein at least one of the deposited layers is rough.

* * * * *